(12) United States Patent
Fulbrook et al.

(10) Patent No.: US 7,874,410 B2
(45) Date of Patent: Jan. 25, 2011

(54) INTRAVENOUS POLE POWER ORGANIZER (IVPPO)

(76) Inventors: Jason D. Fulbrook, 3478 Barrister's Keepe Cir., Fairfax, VA (US) 22031; David J. Fulbrook, 3478 Barrister's Keepe Cir., Fairfax, VA (US) 22031; Jim E. Fulbrook, 3478 Barrister's Keepe Cir., Fairfax, VA (US) 22031

( * ) Notice: Subject to any disclaimer, the term of this patent is extended or adjusted under 35 U.S.C. 154(b) by 593 days.

(21) Appl. No.: 11/984,235

(22) Filed: Nov. 15, 2007

(65) Prior Publication Data

US 2008/0116157 A1   May 22, 2008

Related U.S. Application Data

(60) Provisional application No. 60/859,250, filed on Nov. 16, 2006.

(51) Int. Cl.
*B66C 13/12* (2006.01)
*A47K 1/04* (2006.01)
*H02H 3/22* (2006.01)

(52) U.S. Cl. .................. 191/12 R; 248/129; 361/111
(58) Field of Classification Search .............. 191/12 R, 191/12.2 R, 12.4, 12 S; 248/127–129; 361/54, 361/56, 111, 117, 126, 127
See application file for complete search history.

(56) References Cited

U.S. PATENT DOCUMENTS 7,193,830 B2 *   3/2007   Fournier et al. ............. 361/111
2005/0116126 A1 *   6/2005   Ugent et al. ................ 248/129

* cited by examiner

*Primary Examiner*—S. Joseph Morano
*Assistant Examiner*—Robert J McCarry, Jr.
(74) *Attorney, Agent, or Firm*—John Richardson (57) ABSTRACT

The invention provides an apparatus for safely storing and retrieving power cords and electronic wiring associated with a mobile intravenous pole serving patients in intensive care settings wherein a plurality of devices are required and enabling the patient to be mobile without causing power cords and wiring to become tangled and dragging on patient room or hospital floors.

15 Claims, 5 Drawing Sheets

INTRAVENOUS POLE POWER ORGANIZER (IVPPO)

This application claims priority to U.S. Provisional Application No. 60/859,250 dated Nov. 16, 2006.

STATEMENT REGARDING FEDERALLY SPONSORED RESEARCH OR DEVELOPMENT

Not applicable

REFERENCE TO SEQUENCE LISTING A TABLE, OR A COMPUTER PROGRAM LISTING COMPACT DISC APPENDIX

Not Applicable

BACKGROUND OF THE INVENTION

Recent developments in medical care settings such as intensive care units have shown a significant increase in the number patient sensors, monitors, infusion devices for functions such as ECG respiration rate, non-invasive and internal blood pressure readings, oxygen saturation and carbon dioxide levels, timing pumps, blood pumps, saline drips, syringe pumps, nutrition supplies, etc.

The result of this conglomeration of medical devices is a plurality of power cords and electronic wiring that leads to a mass of tangled cords and wires spread on the hospital room floor that provide a source of contamination and spreading of infections.

It has been reported that cross type bacterial infections in hospital settings are on the increase from categories such as MRSA (methicillin-resistant staphylococcus aureus), VRE (vancomycin-resistant enterococci), ESBL (extended spectrum beta-lactamase), etc., and contribute to an estimated 19,000 fatalities and 80,000 hospital infections per year.

The existing prior art for IV (intravenous) pole arrangements are limited to providing multiple powered devices in the form of electrical surge/power strips that are merely hung from an IV pole wherein each of the powered supply electrical to each of the said devices requires an individual wall power socket outlet. In this environment when a patient requires to be moved or relocated all the power supply outlets must be unplugged with the attachment cords and AC/DC converter plugs hung over the top of the IV pole, which is awkward and inefficient. If any of the power cords touch the floor, they must be thoroughly cleaned prior to re-use, to avoid possible contamination.

Prior art multiple powered infusion hospital systems use IV poles wherein each infusion system requires an individual power outlet plugged into power outlet socket points and each item comprising power cords, AC/DC converter adaptors, requires to be unplugged for each movement of the patient.

To overcome these significant operational limitations and shortcomings in existing prior art in the management and storage of power cords and electronic wiring systems associated with situations such a intensive patient care, the inventive concept described as intravenous pole power organizer (IVPPO) is disclosed hereunder.

The IV Pole Power Organizer (IVPPO) has a multitude of potential applications such as hospital critical care situations, nursing homes, or home health care.

The IVPPO would not require US FDA approval and comprise electrical components that are standard commercially off the shelf (COTS) items, and wherein direct patient intervention and monitoring that impact a patient's status are not applicable for US FDA review requirements.

The IV Pole Power Organizer (IVPPO) has two main components; a unique power strip that attaches to the bottom of a vertical IV pole and a clamp to hold the organizer cord and plug when removed from the wall socket power supply outlet. The IVPPO has six uniquely placed outlets, a hook, an LED light, a USB port outlet, and a flashlight portable or integral power charger that are all configured to provide the maximum patient and care giver ergonomic advantages.

The IVPPO is very useful for patients and care staff because it is convenient and will be affordable. It will keep power cords organized and off the floor and make it easy to move patient because only one plug goes to wall power supply outlet.

There are power strips for electrical devices in prior art but the IVPPO is unique because it has clamps on the back, and a special arrangement of sockets for plug converter boxes used with syringe pumps and other infusion systems. In addition, the invention discloses a flashlight charge socket (as in a cigarette lighter), a plurality of cleats to wrap individual power supply cords, a built-in LED night light that stays on with power loss, a hook for bed pan/urinal, or Foley Catheter Bag or equal appliance, on one side and a separate clamp to secure the IVPPO cord and plug.

SUMMARY OF THE INVENTION

The instant invention is eminently applicable for intensive care patients with neutropenia conditions. Neutropenia is an abnormal decrease in the number of neutrophils type in the blood. White blood cells (neutrophils & leukocytes) are the cells in the blood that play important roles in body's immune system by fighting infection. White blood cells (WBC) can be affected by many diseases and in patient treatment, doctors continuously check WBC counts in evaluating patient health conditions. Neutropenia is present when the neutrophil count is less than an established number, when WBC counts are made. Neutropenia may be seen with viral infections, with some leukemia's, and after radiation therapy or chemotherapy; neutropenia lowers the immunologic barrier to bacterial and fungal infection.

When a person has a disease or undergoes a treatment that lowers WBC count below established levels, the patient, care providers, family members, and visitors must conform to a set of rules and protocols for neutropenic conditions intended to reduce the amount of germs the patient is exposed to. If the patient gets an infection, especially a bacterial or fungus infection that becomes systemic i.e. occurs within the blood stream and internal body, the patient will become very ill and could die in hours if the condition is untreated for even a short period of time. Large doses of IV antibiotics and anti-fungal drugs are typically given when an infection is suspected, such as persistent or high fever spikes.

When a person undergoes chemotherapy to treat cancer and other diseases, the patient typically has a surgery where a tube is inserted through the chest and into the major vein just before it enters the heart. One type of central catheter is called a Broviac and typically comprises two lumen tubes so that multiple fluid medications can be infused at the same time.

When medical professionals state that neutropenic conditions apply, everyone coming in contact with the patient must wash their hands rigorously any time potentially unclean material is handled and each time anyone reenters the patient's room. In particular, food requires special handling procedures. Patients are usually kept in a special private room where positive air pressure and special cleaning procedures are maintained. Medical protocols require that any time an item comes in contact with the floor it must be discarded. If an item cannot be discarded it must be disinfected using strong cleaning agents.

The IVPPO is an effective medical tool because it will greatly improve efficiency and organization of power supply devices on an IV pole. For example, in typical leukemia treatment 4 to 5 devices are used at one time and unplugging so many each time from wall power supply outlet sockets to visit, for example, rest rooms is a major problem as power cable contact with the floor has to be prevented at all times to prevent contamination and spread of infections.

Typical examples of patient medical care infusion devices include but are not limited to blood pumps, timing pumps, saline and nutrition drips, medical monitors, and syringe pumps.

The IVPPO will improve patient care and convenience in hospital, clinic, nursing home and home care settings where IV pole is used with multiple medical devices in the treatment for example, of cancer, transplant, burn units and intensive care patients.

The IVPPO facilitates treatment of specific categories of patients such as, for example, those requiring neutropenic conditions, where keeping medical components from contact with floors.

The instant invention incorporates a flashlight charger, night light LED and hook for urinal/bed pan, Foley type catheter bags, and aids to assist medical care staff and patients by improving organizational of required medical care items.

The instant invention for an IV Pole Power Organizer (IP-PPO) has two principal components comprising a unique power strip that attaches to the base of an IV pole and a holder that clamps onto the said IV pole above a power strip arranged to hold the organizer power cord and a power supply outlet plug when the said power outlet plug is detached from a power supply outlet wall socket.

The instant invention IVPPPO is capable of assisting patients and care providers by organizing a number of power supply powered medical devices that are attached to an IV pole structure, in a manner that only a single power supply plug is required to be powered from wall socket power supply outlets and thereby enables the said IV pole to be maneuvered and moved when the patient requires to be moved.

The said IVPPO of the instant invention is arranged to provide a number of specific capabilities comprising but not limited to, a) at least six uniquely placed power supply outlet connections, b) a plurality of attaching cleats capable of wrapping and securing excess power cord lengths from a plurality of patient care devices, c) a plurality of attachment hooks that are capable of securing patient care items such as, but not limited to, patient urinal and bedpans, Foley type catheter bags, d) a rechargeable LED (light emitting diode), night light to illuminate the patient environment, e) a rechargeable power supply charger plug for a standard commercially available off-the-shelf LED flashlight to assist in patient care, and a USB port for recharging electronic devices such as PDAs MP3 players, IPhones, and IPODs.

REFERENCE OF NUMERALS USED IN FIGURES

The table below lists all of the reference numerals employed in the Figures, and identifies the element designated by each numeral 30 COTS Telescopic IV pole element
32 COTS IV pole cast iron roller supports
34 Power cord holder made of resilient flexible material
36 Clamps
38 Wing nut bolt fasteners
40 Customized power supply cord housing with pressure suppression unit
42 Snap-on clip
44 Removable protection canopy
46 Key-hole hook
48 Power supply sockets
50 Cleats
52 USB port
54 Surge suppression unit on/off switch
56 Surge suppression circuit-breaker reset button
58 LED (light emitting diode) unit
60 COTS type LED flashlight
62 COTS type rechargeable power supply receptacle
64 Typical AC/DC converter unit for an infusion device connected with the surge suppression unit 40
66 Insulating and bumper pad
68 Power supply cord to surge suppression unit 40
70 A detachable or internal power rechargeable battery charging unit that will provide for all or most of the systems connected to the surge suppression unit 40 to operate for a limited period of time of at least 30 minutes in the event of a temporary power failure.

DESCRIPTION OF THE PREFERRED EMBODIMENTS

The instant invention incorporates a number of elements that can be categorized commercially off the shelf and these are identified accordingly as COTS.

The instant invention comprises a standard 7 foot high COTS IV telescopic pole structure 30 with cast iron roller supports 32 and it is upon this structure that the inventive concept elements are attached.

The essential novel elements of the instant invention comprise a power cord holder 34 attached by clamps 36 that are sized to connect with both diameters of said telescopic IV pole 30 attached by wing nut fasteners 38 to the said IV pole 30, a customized power cord housing with supply surge suppression unit 40 attached to the said IV pole 30 by a snap-on clip 42, and a removable protection canopy 44 also attached to the said IV pole 30.

The said customized power supply surge suppression unit 40 comprises a plurality of novel features that provide for enhanced patient care and ease of care giver nursing operations. Specifically, each of these features is described in the following.

An externally attached hook 46 with a key-hole for the purpose of supporting a urinal, bed-pan or Foley type catheter bag.

A plurality of power supply outlet sockets 48 integral with and strategically located on the face of the said surge suppression unit 40 to effect the maximum patient comfort and care giver ease of operation.

A plurality of cleats 50 externally attached to the said surge suppression unit 40 and located for maximum patient comfort and care giver ease of operation.

An USB signal port 52 positioned integral with the said surge suppression unit 40 for the purposes of recharging devices such as PDA,s, MP3 player, iPods or equal electronic devices.

Surge suppression unit on/off switch 54.

Surge suppression unit circuit-breaker reset button 56.

Integral LED (light emitting diode) 58 recessed at the top corner of the said surge suppression unit 40.

Removable COTS LED (light emitting diode) flashlight 60 powered from a COTS type rechargeable power supply connection 62 integral with the said surge suppression unit 40.

Positioning of typical COTS type AC/DC power converter unit 64 connected to the said power suppression unit 40.

Positioning of an insulating/bumper pad 66 between the bottom surface of said power suppression unit 40 and the IV pole support 32.

Power supply cord 68 to the surge suppression unit 40 is arranged for a total length optimized to suit the standard elevation of hospital wall electrical socket power outlet and a workable distance between the said wall socket and the patient location.

The instant invention of the IVPPO comprises two essentially novel features that are fundamental in achieving the very significant advantages over existing prior art power suppression units, and these have been identified earlier as the power cord holder 34 and the customized power cord housing with supply pressure suppression unit 40.

The said power cord holder assembly 34 is arranged for an optimum positioning elevation on the telescopic pole element 30 in a manner that a) lines up horizontally with standard hospital power supply wall sockets and provides a workable cable reach from the said wall socket to the residing location of the IV pole 32 relative to the patient.

The vertical location of the power cord holder assembly 34 on the approximate 7 foot extended length IV pole member 30, is optimally between 3 to 4 feet above the floor level. In this manner the overall length of the power supply cord 68 for a hospital application of the IVPPO instant invention would be approximately 10 feet.

Figure 1:
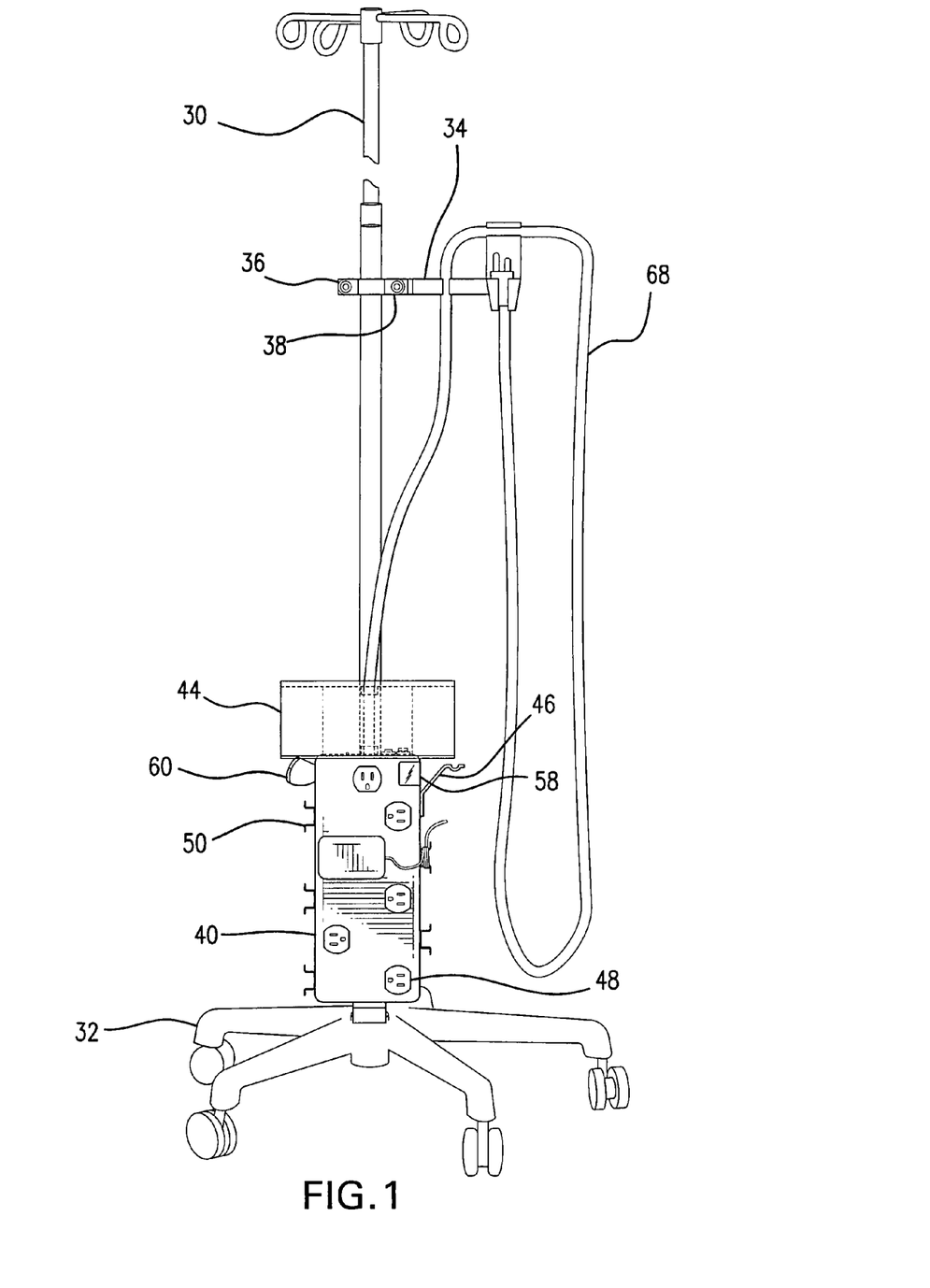
FIG. 1—Shows the overall structure of the IVPPO

As will be evident from FIG. 1, the power supply cord 68 is retained in a safe storage position within the cord holder assembly 34 during occasions wherein the patient is mobile and transports the IVPPO of the instant invention.

Figure 6:
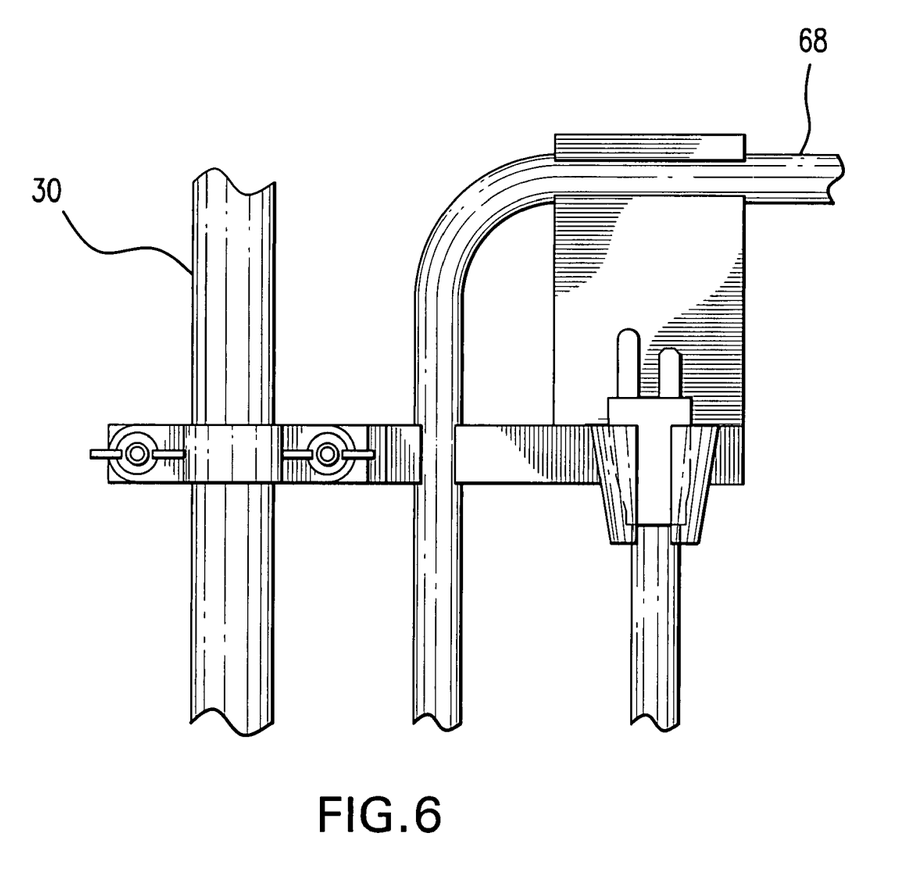
FIG. 6—Shows the side view of the power cord holder 34

It will be clear from FIG. 6 that the cord holder assembly 34 comprises a plurality of features to achieve the desired invention objectives and by way of enabling disclosure these are identified in the following:

1. The main body is formed of a resilient material such as flexible hard rubber or equivalent pliant materials.
2. The cord holder assembly 34 is connected to the IV pole 30 by a semi-circular shaped bracket that is adaptable to both tubular diameters of the telescopic pole 30 and the said bracket is fastened by means of a pair of wing nut headed bolts.
3. The power cord 68 is restrained in both vertical and horizontal planes by means of pliable slot openings engaged by a pressing hand action.
4. The power cable plug head is restrained in a vertical storage position by means of a pliable conical cup feature and is engaged by a pressing hand action.

Figure 2:
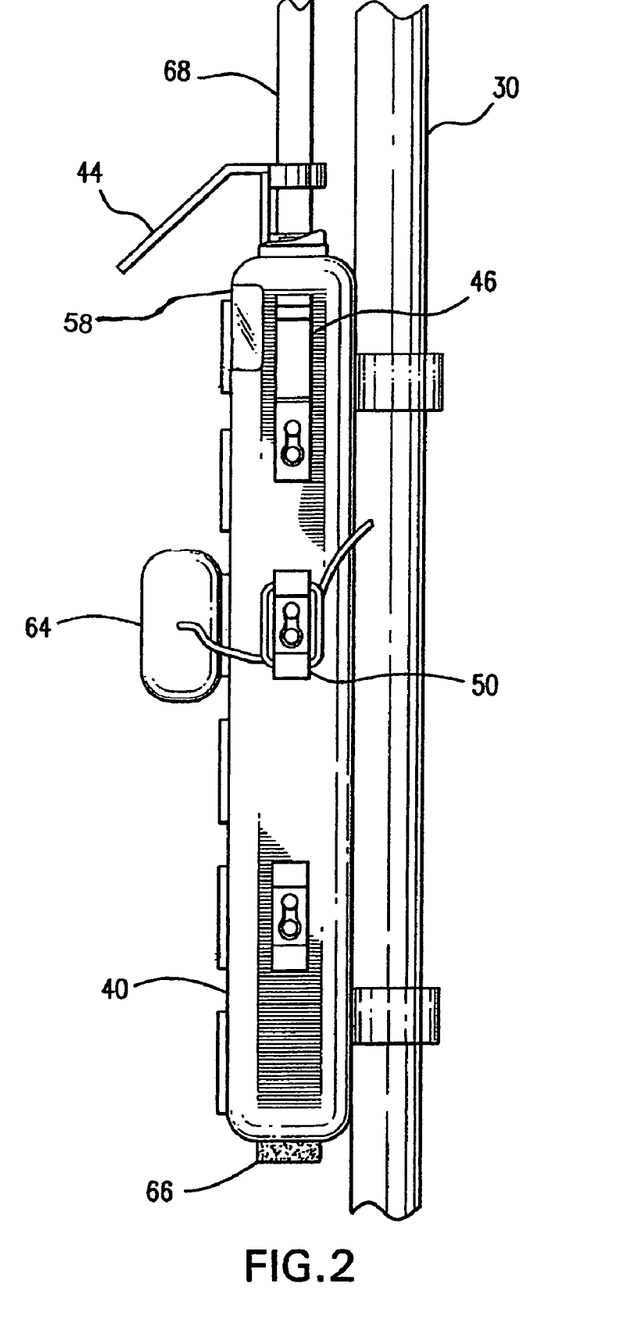
FIG. 2—Shows a side view of the power cord housing surge suppression unit 40
Figure 3:
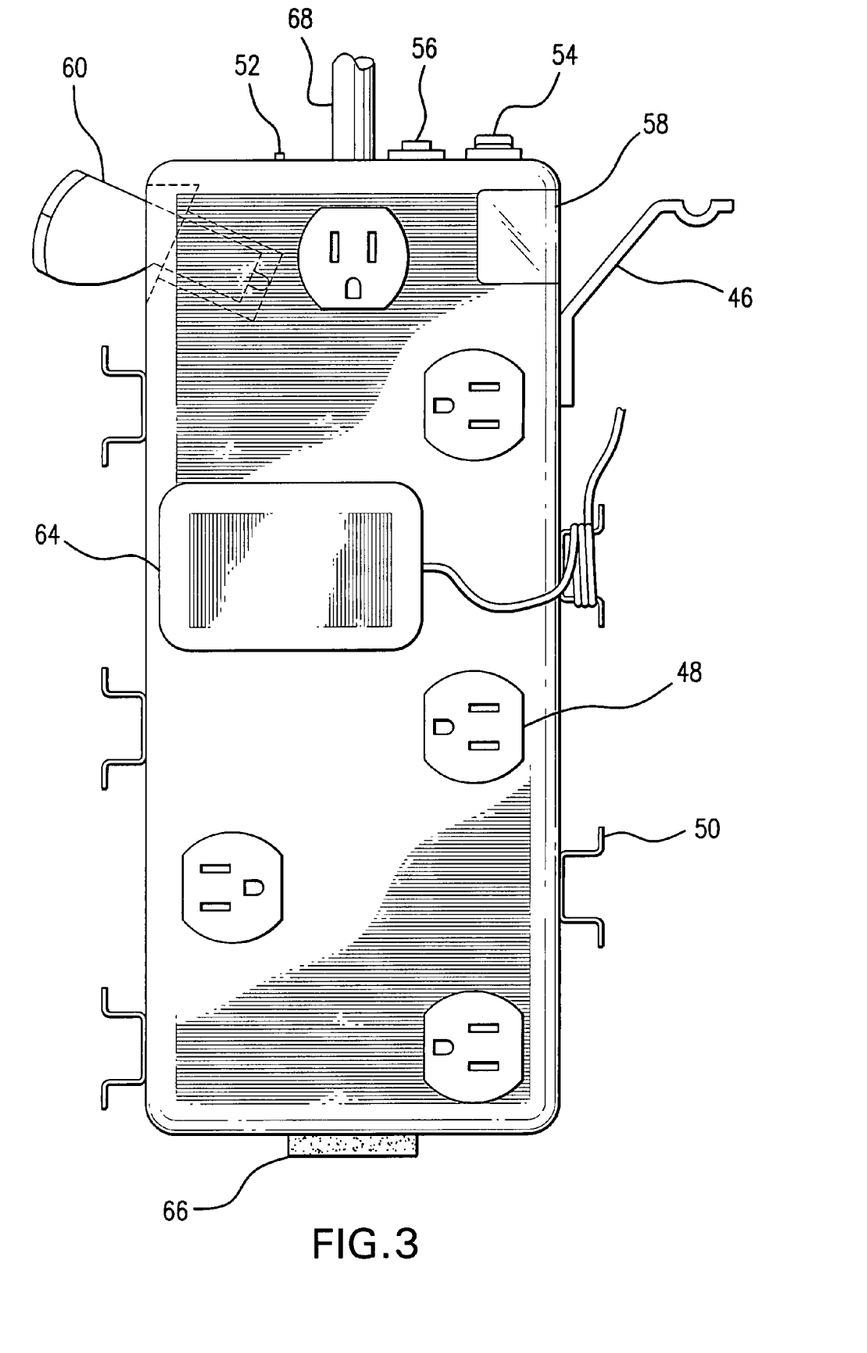
FIG. 3—Shows the configuration of the customized power cord housing surge suppression unit 40
Figure 4:
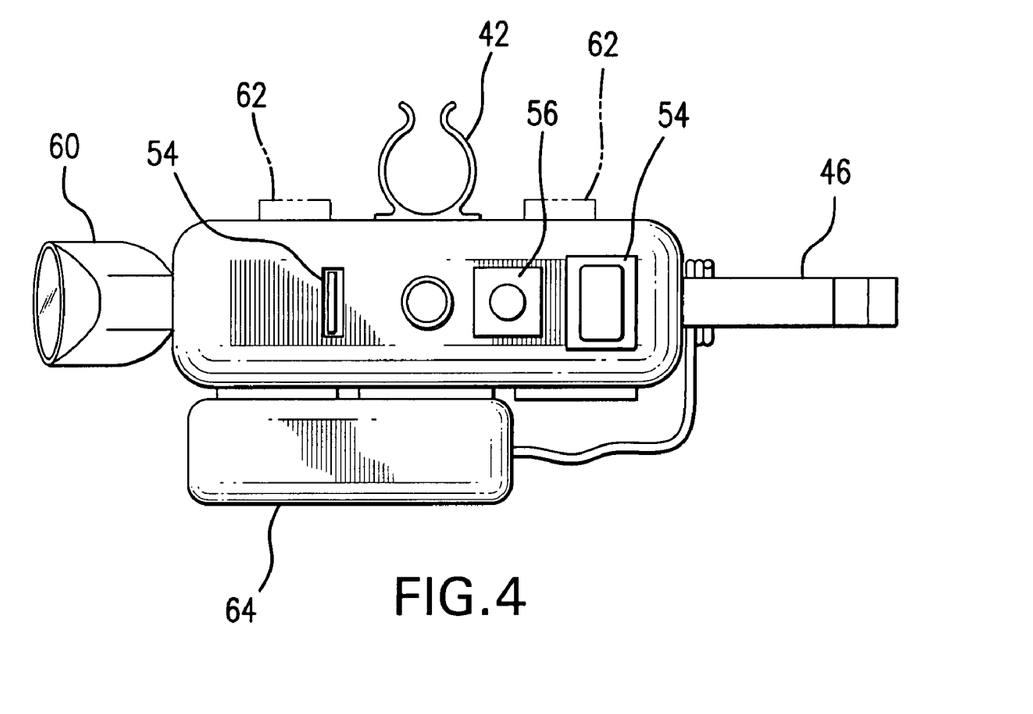
FIG. 4—Shows the top view of the power cord housing surge suppression unit 40
Figure 5:
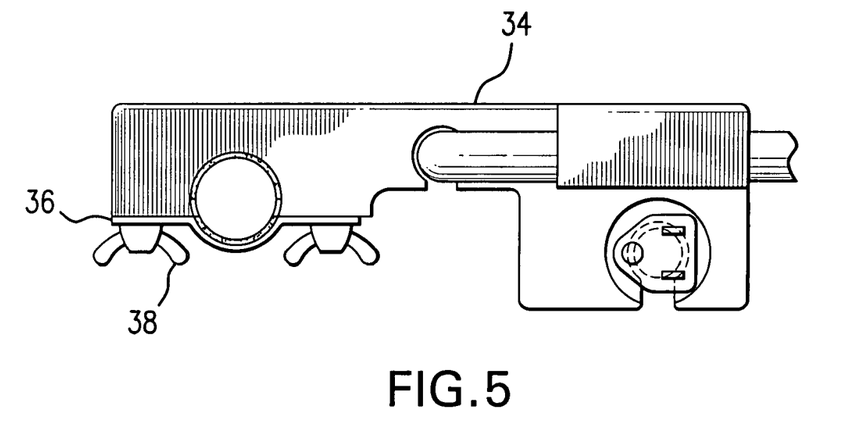
FIG. 5—Shows the plan view of the power cord holder 34

The said power surge suppression unit 40 consists of standard COTS type main body made from materials exhibiting non surface oxidizing properties in the form of stainless steel, titanium, hardened plastic, glass reinforced plastic, aluminum, metallic or other equivalent materials that can be readily sterilized, disinfected, and decontaminated, and comprises as a minimum the following elements:

1. As will be apparent from FIGS. 1 & 4, the said unit 40 is connected to the said IV pole 30 by means of a spring loaded slip-on clip 42 that is attached to the external rear surface of the main body.
2. The power supply cord 68 enters the top surface of the main body through a standard UL label regulation type COTS electrical power fitting.
3. An on/off electrical power switch 54 and a circuit breaker reset switch 56 are positioned on the top surface of the main body on one side of the power cord 68 entry location.
4. At the upper end and part way down from the top surface of the main body side surface, an angled keyhole hook type support 46 with a semi-circular indent is attached for the purposes of supporting a variety of utensils including but not limited to, a urinal, a bed-pan, and/or a Foley type catheter bag.
5. In a recess at the top corner of the main body is located an LED (light emitting diode) illumination means 58 that is re-chargeable through a standard COTS internal electrical wiring connection within the main body.
6. In an angled recess at the top corner of the main body unit, a removable 12 volt DC LED (light emitting diode) flashlight 60 is stored and powered through a standard COTS automobile cigarette lighter type device, and the assigned angle of approximately 30 degrees to the horizontal plane is selected for ease of retrieval and replacement.
7. At the bottom surface of the main body is placed a hard rubber or equal material pad 66 interposed between the said main body and the IV pole support 32.
8. Positioned on the top surface of the main body of the main body 40 there is a USB port 52 rated at approximately 5 volts for the purposes of recharging portable electronic devices including but not limited to PDA's, MP3 players, IPhones and Ipods.
9. A minimum of six (6) standard 115 volt AC power supply outlets 48 are located on the front face of the main body and powered from the incoming power supply cord 68. The relative location of these outlets and positioning between outlets is predicated on providing adequate spaces for AC/DC converter boxes and the orientation of the outlet plug pin openings line up with associated cleats positioned on the side surfaces of the main body in a manner that facilitates safely retaining excess low voltage (3-5 volt DC) wiring cable.
9. Attached at the upper surface face of the main body as shown in FIGS. 1 & 2, is placed a removable protection canopy 44 for the purposes of preventing any discharge fluids from entering any of the electrical openings in the said surge suppression unit 40.

A detachable or internal power charging unit 70 is connected to the surge suppression unit 40 and provides for all or most of the systems connected to the said surge suppression unit 40 to operate for a limited period of time of at least 30 minutes in the event of a failure of power supply.

Power cable holder assembly 34 is made from materials such as, resilient hardened rubber, hardened plastic and equal material exhibiting properties of resilience and flexibility.

The power sockets 48 are arranged in a manner wherein the two electrical conductive prongs and the ground prong are in alignment with an associated cable cleat 50 to facilitate the collecting of excess cable to preclude trailing the cable on the floor of the patient room.

The instant invention is novel in the configuration of the power cable supply cord 68 in relation to the position on the COTS IV pole 30 based on the avoidance of allowing the cable to come into contact with the hospital floor leading to the spread of infections. Specifically the instant invention as disclosed in FIG. 1 has determined an optimum length of cable 68 approximately 9 feet based on a height of approximately 4 feet above the floor to the power cable cord holder 34, accommodate a 6 foot distance from the IV pole 30 to the hospital wall power socket, and allowing for double loops in the stored position when in the mobile configuration. The selected range of power cord cable 68 provide for variations in COTS IV telescopic pole heights.

The power cord organizer apparatus of the instant invention for mounting to a portable COTS type intravenous (IV) pole assembly specifically comprises i) a power cord housing with a rear portion, opposing side portions, a front portion, and upper and lower portions, the front portion of the power cord housing sized to contain at least six 115 volt electrical sockets in a spaced relation thereon, ii) a plurality of cable retainers, each cable retainer secured to one of the opposing side portions of the power cord housing in alignment with a selected one of the at least six electrical sockets, each cable retainer sized to wind a power cord thereon to keep the power cord(s) from touching the floor, iii) an attachment clip for releasably securing the back side of the power cord housing to the portable COTS type intravenous (IV) pole assembly; and, iv) a surge suppression unit mounted within the power cord housing, the surge suppression unit including an on/off switch and a re-set button positioned on the upper portion of the power cord organizer, v) an integral power charging unit is mounted in the power cord organizer, and the integral power charging unit is capable of providing at least 30 minutes of standby power for connected appliances, vi) a power cord holder for supporting a power cord above a patient room floor including a bracket for receiving the end of the power cord during transport, and vii) a light emitting diode (LED) illumination means mounted to the front portion of the power cord housing.

In a further particular the instant invention is novel and unique in the layout of the customized power supply pressure suppression unit 40 to arrive at a configuration of power outlet positions to provide optimum ergonomic ease of attachment of infusion devices 64 and organization of cables and wiring to prevent contact with hospital floors and hazards of loose cables and wiring leading to foot tripping potential and general fire hazards. In a typical configuration of treatment in a neutropenia environments there could be a requirement of six power outlets 48 with one dedicated to a 115 volt pump unit, and four for infusion converter units, and one pain relief unit. In the instant invention, the top socket 48 is dedicated to the said 115 volt pump unit as shown in FIG. 1 with the ground pin pointing downwards with the cable cleat for the supply cord formed as part of the said pump unit. The remaining sockets 48 as disclosed in FIG. 1 are uniquely arranged with the ground pin oriented in the horizontal plane and facing the cleat 50 so that the low voltage cable can be secured in a tidy manner as shown in FIG. 1 for a typical infusion converter unit 64.

It will be obvious to one of ordinary skill in the art that the inventive concept of the instant invention is also applicable for the management and storage of electrical and electronic power and instrument cords in an office setting, home entertainment centers, at desk workstations, stereo and video and game-boy stations, laboratory work stations, wherein electrical power supplies from an AC power plug socket to the individual locations and associated printers, audio speakers, computer keyboards, telephone and fax machines, and printers, involve a plurality of power cords and ancillary low voltage wiring that require to be kept tidy and avoid spreading around the floor areas in a manner conducive to creating accident and fire hazard environments.

It will also be evident to one of ordinary skill in the art that the disclosed inventive concept for a customized power supply suppression unit has multiple other applications in settings requiring controlled clean conditions including but not limited to a) radioactive facilities in the areas of nuclear fuel manufacture, nuclear power operating facilities, nuclear decommissioning and decontamination facilities, b) automotive repair and maintenance facilities subject to excessive releases of fluids on the operating floors, etc., and c) manufacturing facilities for the production of electronic solid state devices where the establishment and maintenance of operational clean conditions is essential.

It will be evident to those skilled in the art that other changes and modifications from those disclosed herein are possible. The instant invention therefore should not be considered limited to the examples selected for the purpose of illustration, and should be viewed as including all changes and modifications which do not constitute a departure from the essential inventive concept and scope of the instant invention as claimed in the foregoing claims and such equivalents as may be considered appropriate.

We claim:

1. A power cord organizer apparatus for mounting to a portable COTS type intravenous (IV) pole assembly, which comprises: and,
   a) a power cord housing with a rear portion, opposing side portions, a front portion, and upper and lower portions, the front portion of the power cord housing sized to contain at least six 115 volt electrical sockets in a spaced relation thereon; and,
   b) a plurality of cable retainers, each cable retainer-secured to one of the opposing side portions of the power cord housing in alignment with a selected one of the at least six electrical sockets, each cable retainer sized to wind a power cord thereon to keep the power cord(s) from touching the floor; and,
   c) an attachment clip for releasably securing the back side of the power cord housing to the portable COTS type intravenous (IV) pole assembly; and,
   d) a surge suppression unit mounted within the power cord housing, the surge suppression unit including an on/off switch and a re-set button positioned on the upper portion of the power cord organizer; and,
   e) the power cord organizer apparatus further comprises a light emitting diode (LED) illumination mounted to the front portion of the power cord housing and located in a recess at the top corner of the surge suppression unit; and,
   f) a portable flashlight is removably positioned in a recessed indent in one of the sides of the power cord housing and is capable of being recharged from a power supply integral to the surge suppression unit.

2. The power cord housing apparatus of claim 1, wherein an integral power charging unit is mounted in the power cord organizer, and the integral power charging unit is capable of providing at least 30 minutes of-standby power for connected appliances.

3. The power cord organizer apparatus of claim 1, wherein a USB port for recharging appliances selected from a group comprising of PDA's, MP3 players, Iphones and Ipods, or equal electronic devices is mounted to the power cord organizer housing.

4. The power cord organizer apparatus of claim 1, wherein a power cord holder is mounted to the portable COTS type intravenous (IV) pole assembly above the power cord organizer at a location approximately four feet above the patient room floor, the power cord organizer for supporting the power cord above-the floor, and including a bracket for receiving the end of the power cord during transport.

5. The power cord organizer apparatus of claim 1, wherein a detachable protection canopy is mounted above the power cord housing to prevent liquid entry into electrical circuitry located in the power cord housing.

6. The power cord apparatus of claim 1, wherein the power cord housing is made of materials in the form of stainless steel, metallic alloy steels and equal materials exhibiting non surface oxidizing properties.

7. The power cord apparatus of claim 1, wherein the power cord holder is made from materials in the form of hardened rubber and equal materials exhibiting resilience and flexibility properties.

8. A power cord organizer apparatus for mounting to a portable COTS type intravenous (IV) pole assembly, which comprises:
   a) a power cord housing with a rear portion, opposing side portions, a front portion, and upper and lower portions, the front portion of the power cord housing sized to contain at least six 115 volt electrical sockets in a spaced relation thereon; and,
   b) a plurality of cable retainers, each cable retainer secured to one of the opposing side portions of the power cord housing in alignment with a selected one of the at least six electrical sockets, each cable retainer sized to wind a power cord thereon to keep the power cord(s) from touching the floor; and,
   c) an attachment clip for releasably securing the back side of the power cord housing to the portable COTS type intravenous (IV) pole assembly; and,
   d) a surge suppression unit mounted within the power cord housing, the surge suppression unit including an on/off switch and a re-set button positioned on the upper portion of the power cord organizer; and,
   e) an integral power charging unit is mounted in the power cord organizer, and the integral power charging unit is capable of providing at least 30 minutes of standby power for connected appliances; and
   f) the power cord organizer apparatus further comprises a light emitting diode (LED) illumination mounted to the front portion of the power cord housing and located in a recess at the top corner of the surge suppression unit; and,
   g) a portable flashlight is removably positioned in a recessed indent in one of the sides of the power cord housing and is capable of being recharged from a power supply integral to the surge suppression unit.

9. The power cord organizer apparatus of claim 8, wherein a USB port for recharging appliances selected from a croup comprising of PDA's, MP3 players, (phones and Ipods, or equal electronic devices is mounted to the power cord organizer housing.

10. The power cord organizer apparatus of claim 8, wherein a power cord holder is mounted to the portable COTS type intravenous (IV) pole assembly above the power cord organizer at a location approximately four feet above the patient room floor, the power cord organizer for supporting the power cord above the floor, and including a bracket for receiving the end of the power cord during transport.

11. The power cord apparatus of claim 8, wherein the power cord housing is made of materials in the form of stainless steel, metallic alloy steels and equal materials exhibiting non surface oxidizing properties.

12. The power cord apparatus of claim 8, wherein the power cord holder is made from materials in the form of hardened rubber and equal materials exhibiting resilience and flexibility properties.

13. A power cord organizer apparatus for mounting to a portable COTS type intravenous (IV) pole assembly, which comprises:
   a) a power cord housing with a rear portion, opposing side portions, a front portion, and upper and lower portions, the front portion of the power cord housing sized to contain at least six 115 volt electrical sockets in a spaced relation thereon; and,
   b) a plurality of cable retainers, each cable retainer secured to one of the opposing side portions of the power cord housing in alignment with a selected one of the at least six electrical sockets, each cable retainer sized to wind a power cord thereon to keep the power cord(s) from touching the floor; and,
   c) an attachment clip for releasably securing the back side of the power cord housing to the portable COTS type intravenous (IV) pole assembly; and,
   d) a surge suppression unit mounted within the power cord housing, the surge suppression unit including an on/off switch and a re-set button positioned on the upper portion of the power cord organizer, and,
   e) an integral power charging unit is mounted in the power cord organizer, and the integral power charging unit is capable of providing at least 30 minutes of standby power for connected appliances; and,
   f) the power cord organizer apparatus further comprises a light emitting diode (LED) illumination mounted to the front portion of the power cord housing and located in a recess at the top corner of the surge suppression unit; and,
   g) a portable flashlight is removably positioned in a recessed indent in one of the sides of the power cord housing and is capable of being recharged from a power supply integral to the surge suppression unit.

14. The power cord organizer apparatus of claim 13, wherein a USB port for recharging appliances selected from a group comprising of PDA's, MP3 players, Iphones and Ipods, or equal electronic devices is mounted to the power cord organizer housing.

15. The power cord organizer apparatus of claim 13, wherein a power cord holder is mounted to the portable COTS type intravenous (IV) pole assembly above the power cord organizer at a location approximately four feet above the patient room floor, the power cord organizer for supporting the power cord above the floor, and including a bracket for receiving the end of the power cord during transport.

* * * * *